United States Patent [19]

Salyer et al.

[11] Patent Number: 5,299,893
[45] Date of Patent: * Apr. 5, 1994

[54] DISPOSABLE SURGICAL CUTTERS

[75] Inventors: Paul E. Salyer; Brian D. Salyer, both of Warsaw, Ind.

[73] Assignee: Othy, Inc., Warsaw, Ind.

[ * ] Notice: The portion of the term of this patent subsequent to Mar. 31, 2009 has been disclaimed.

[21] Appl. No.: 858,934

[22] Filed: Mar. 27, 1992

Related U.S. Application Data

[63] Continuation-in-part of Ser. No. 668,926, Mar. 13, 1991, Pat. No. 5,100,267.

[51] Int. Cl.⁵ .............................................. A61B 17/16
[52] U.S. Cl. ........................................ 407/54; 407/61; 606/79; 408/207

[58] Field of Search ............................. 606/79–81, 606/84–89; 408/207, 227; 407/53, 54, 61–63

[56] References Cited

U.S. PATENT DOCUMENTS

| 4,116,200 | 9/1978 | Braun et al. | 606/81 |
| 4,811,632 | 3/1989 | Salyer | 76/101 A |
| 5,100,267 | 3/1992 | Salyer | 407/61 X |

*Primary Examiner*—Steven C. Bishop
*Attorney, Agent, or Firm*—Lundy & Associates

[57] ABSTRACT

A disposable cutter which has a plurality of cutting edges. The cutter has perforations adjoining the cutting edges. The cutter defines an axis of rotation. The cutter is joined to a transparent bowl. The bowl is concentric with the axis of rotation. The bowl has a bottom tool driver opening concentric with the axis of rotation.

19 Claims, 2 Drawing Sheets

DISPOSABLE SURGICAL CUTTERS

CROSS REFERENCES TO RELATED APPLICATIONS

This is a continuation in part of co-pending application Ser. No. 07/668,926 filed on Mar. 13, 1991, now U.S. Pat. No. 5,100,267.

BACKGROUND OF THE INVENTION

The present invention pertains to surgical cutters and more particularly pertains to disposable surgical cutters such as acetabular reamer cups and patella cutters.

Acetabular reamers are surgical tools, which are used to cut hemispherical cavities in pelvis bones for the insertion of artificial hip joints. An acetabular reamer is composed of an acetabular reamer cup mounted on a tool driver, which in turn is mounted in the chuck or collet of a portable drill or flexible powered shaft. Acetabular reamer cups have a complex arrangement of precisely shaped cutting surfaces extending outwardly from an essentially hemispherical shell. Acetabular reamer cups are separable from their tool drivers for changing cup size prior to or during surgery, cleaning, and/or sharpening.

Acetabular reamers must be capable of producing cavities with very close tolerances. Both acetabular reamers and patella cutters must also minimize any risk of causing contamination and be light in weight and fit on an appropriate tool driver with a minimum of free play quickly and easily without tools. Prior acetabular reamer cups and patella cutters must be cleaned after each use. Thus, the desirability of a disposable reamer cup and cutter.

Some previous acetabular reamers have used an openbottom acetabular reamer cup gripped by the tool driver by means of a flange and slot and an opposed springloaded ball catch, like that on a socket wrench or socket driver. This presents a problem in that the catch tends to trap dried blood, which is very difficult to remove during cleaning. An additional problem is that unless tolerances of cups and tool drivers are made very close, at great cost, there is considerable free play between a cup and its tool driver. This increases wear and decreases the precision of the tool.

An alternative acetabular reamer, described in U.S. Pat. No. 4,811,632, utilizes a convex-bottomed acetabular reamer cup having a large central opening complementary in shape to a flange on the tool driver. Since the tool driver also grips the cup with a clamping action, extremely close tolerances are not required to prevent free play between the cup and driver. The convex bottom of the cup eliminates any internal ninety degree angles which could catch contaminants and the large central opening permits easy cleaning. The acetabular reamer cup is, however, complex in shape and expensive and, like all acetabular reamer cups, difficult to resharpen and must be cleaned between uses.

Patella cutters are surgical tools, similar in some respects to acetabular reamer cups, which are used to cut or shaped the under side of the patella or knee cap as desired. A patella cutting system is generally composed of a cutter mounted on a tool driver, which in turn is mounted in the chuck or collet of a portable drill or flexible powered shaft. Cutters for patella have a complex arrangement of precisely shaped cutting edges extending outwardly from a flat planer surface. Cutters are separable from their tool drivers for changing cutter size prior to or during surgery, cleaning, and/or sharpening.

Unique to knee surgery and some hip operations is the utilization of milled bone, tissue and debris as filler to be placed between the artificial insert and the body to assist the healing process. Thus, prior patella cutting systems provide a hollow, opaque interior cavity for retaining bone debris, like that described in allowed U.S. patent application Ser. No. 07/851,504 filed on Mar. 16, 1992, entitled Patella Cutting System. The cutters described therein, however, are suited for use only in conjunction with the accompanying tool driver also described therein and each is composed of highgrade steel. This presents a problem in that the cutting lids cannot be rotatably driven by a number of different tool drivers and the cost of manufacturing the matching tool drivers and cutting lids is unnecessarily excessive. Also, with the tool drivers disclosed, the operator cannot usually see the accumulation of bone debris through the back of the driver as is desired.

It is therefore highly desirable to provide an improved acetabular reamer cup and patella cutter.

It is also highly desirable to provide an improved acetabular reamer cup and patella cutter which are disposable and fit on a tool driver with a minimum of free play.

It is also highly desirable to provide an improved acetabular reamer cup and patella cutter which are disposable and precise in size, light in weight and inexpensive.

It is also highly desirable to provide an improved acetabular reamer cup and patella cutter which are disposable and quick and easy to install and remove from a tool driver without tools.

It is finally highly desirable to provide an improved acetabular reamer cup and patella cutter which meet all of the above desired features.

SUMMARY OF THE INVENTION

It is an object of the invention to provide an improved acetabular reamer cup and patella cutter.

It is another object of the invention to provide an improved acetabular reamer cup and patella cutter which are disposable and fit on a tool driver with a minimum of free play.

It is another object of the invention to provide an improved acetabular reamer cup and patella cutter which are disposable and precise in size, light in weight and inexpensive.

It is another object of the invention to provide an improved acetabular reamer cup and patella cutter which are disposable and quick and easy to install and remove from a tool driver without tools.

It is finally an object of the invention to provide an improved acetabular reamer cup and patella cutter which provide all of the above objects.

In the broader aspects of the invention there is provided a disposable cutter which has a plurality of cutting edges. The cutter has perforations adjoining the cutting edges. The cutter defines an axis of rotation. The cutter is joined to a transparent bowl. The bowl is concentric with the axis of rotation. The bowl has a bottom tool driver opening concentric with the axis of rotation.

BRIEF DESCRIPTION OF THE DRAWINGS

The above mentioned and other features and objects of the invention and the manner of attaining them will become more apparent and the invention itself will be better understood by reference to the following description of an embodiment of the invention taken in conjunction with the accompanying drawings wherein.

DESCRIPTION OF A SPECIFIC EMBODIMENT

Figure 1:
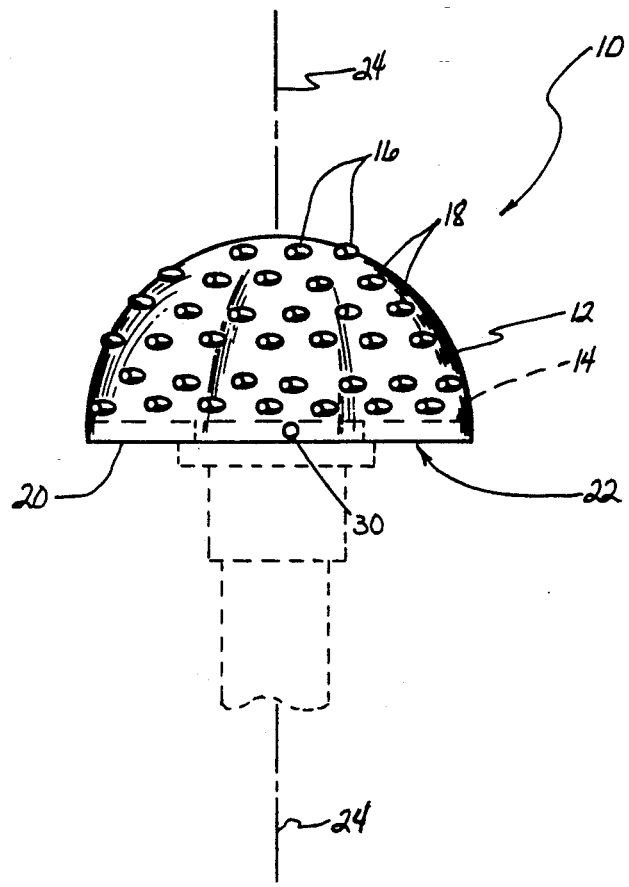
FIG. 1 is a perspective view of an embodiment of the disposable acetabular reamer cup of the invention.

The disposable acetabular reamer cup 10 of the invention has a cutting bowl 12 and a plug 14. Cutting bowl 12 is substantially hemispherical in shape and has a spirally arranged pattern of outwardly extending cutting edges 16 and adjoining perforations 18. Cutting bowl 12 has a periphery 20 surrounding a bottom opening 22. Cutting bowl 12 defines an axis of rotation 24, which is perpendicular to a plane defined by periphery 20. In a particular embodiment, the material of cutting bowl 12 is 19 gauge (0.040") 410 surgical stainless steel, and both the bowl 12 and the cutting edges 16 are formed as disclosed in U.S. Pat. No. 4,811,632, the specification of which is incorporated herein by reference.

Plug 14 occupies bottom opening 22 and is joined to cutting bowl 12. Plug 14 is concentric with axis of rotation 24. Plug 14 defines, in combination with cutting bowl 12, a hollow cup chamber 26. Plug 14 has a tool driver opening 28 concentric with the axis of rotation 24. In a particular embodiment of the invention, plug 14 is circular and fits tightly within cutting bowl opening 22, adjoining periphery 20, and tool driver opening 28 is hexagonal in shape. Tool driver opening 28 is concentric with axis of rotation 24.

Plug 14 is retained in bottom opening 22, in a fixed position, by detents 30 and complementary intrusions 32. Each detent 30 is an inwardly extending portion of cutting bowl 12, which is staked, punched, embedded or driven into the intrusions 32 of plug 14. Plug 14 is joined to cutting bowl 12 solely by detents 30 and intrusions 32 and the friction between the cutting bowl 12 and the plug 14. In a particular embodiment of the invention, two to six equally separated detents 30 positioned adjacent to periphery 20 extend inwardly in a direction radial to axis of rotation 24 to a distance from about 0.020" to about 0.040".

Figure 3:
FIG. 3 is a cross-sectional view of one plug of the disposable acetabular reamer cup of the invention taken diametrically.
Figure 4:
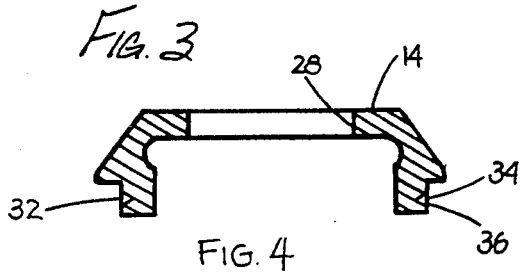
FIG. 4 is a cross-sectional view of another plug of the disposable acetabular reamer cup of the invention like FIG. 3 taken diametrically.
Figure 6:
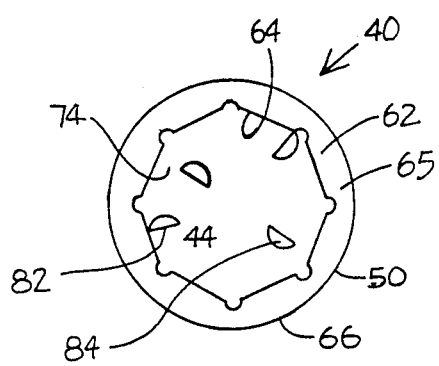
FIG. 6 is a bottom plan view of the disposable patella cutter of the invention.
Figure 7:
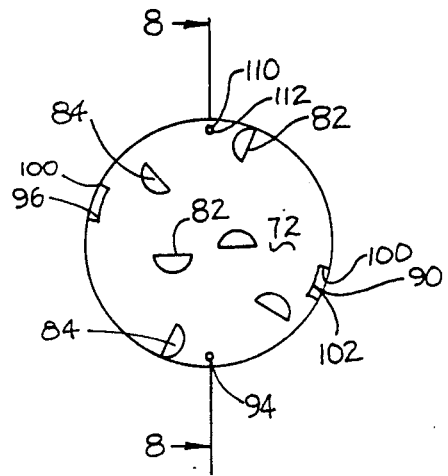
FIG. 7 is a top plan view of the disposable patella cutter of the invention.
Figure 5:
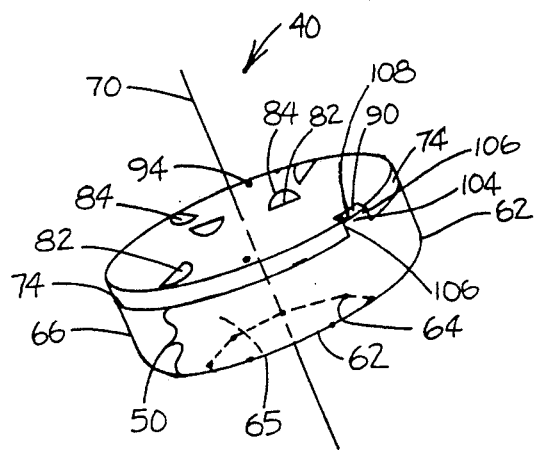
FIG. 5 is a side perspective view of a disposable patella cutter of the invention.
Figure 8:
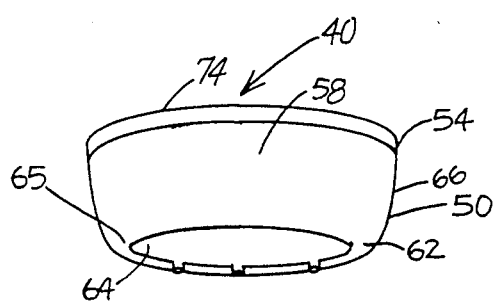
FIG. 8 is a cross-sectional view of the disposable patella cutter of the invention as shown in FIGS. 6 and 7 taken substantially along the section line 8—8 in FIG. 7.

Plug 14 is molded of a polymeric material. In a particular embodiment, plug 14 is a disk of a uniform thickness with circular cross-sections taken transversely to its axis. In another particular embodiment, plug 14 may have cross-sections taken axially of a variety of shapes. In one particular embodiment, disk 14 in cross-sections taken axially, disk 14 is of uniform thickness. In another particular embodiment, disk 14 in cross-sections taken axially, is thicker adjacent driver opening 28 and periphery 20. In this particular embodiment, a portion of disk 14 between opening 28 and periphery 20 is "necked" down in cross-section thereby providing easy viewing into the interior of the reamer cup through plug 14 at all times. See FIG. 3. In another particular embodiment, as shown in FIG. 4, plug 14 has a cross-sectional shape of a disk with a conical frustum coaxially joined together.

Figure 2:
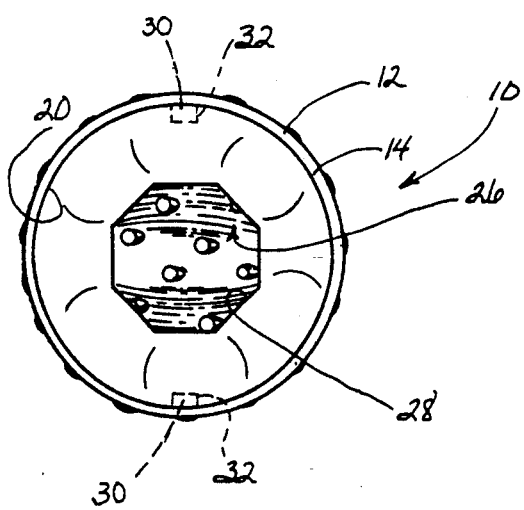
FIG. 2 is a bottom plan view of the disposable acetabular reamer cup of FIG. 1.

Plug 14 is molded so as to form the intrusions 32 in the outer periphery 20. Protrusions may range from two diametrically opposed intrusions to six equally spaced or three pairs of diametrically opposed protrusions in the periphery 20. In a preferred embodiment, each of the protrusions from a top plan view have a rectangular shape with two opposed ninety degree angles as shown in FIG. 2 in dashed lines. The protrusions of this same preferred embodiment, when viewed in cross-sections taken axially of plug 14, have a triangular cross-section with a planar sloping wall 34 extending from adjacent the periphery 20 inwardly and a planar orthogonal wall 36 extending generally parallel to the top and bottom surfaces of plug 14. Thus, intrusions 32 of this embodiment are wedge shaped. As shown in FIG. 2, the detents 30 positioned within intrusions 32 substantially fill the intrusions 32.

In a particular embodiment, the plug 14 is formed of polycarbonate material. Plug 14 when in the shape of a disk is approximately ⅛" thick. In all embodiments of the acetabular reamer cup of the invention, each detent 30 is formed by staking, punching or driving the metal of the cutting bowl 12 overlaying the intrusions 32 into the intrusions 32 thereby deforming the metal into the void of the intrusion 32 substantially filling the void of the intrusion 32 and forming a detent of a similar shape to the shape of the intrusion 32.

The polycarbonate material of plug 14 which is strong, lightweight, and transparent, having high temperature and impact resistance. An example of such a material is a polycarbonate sold under the trademark LEXAN by E. I. Dupont de Nemours and Company.

The disposable acetabular reamer cup 10 of the invention is used in the same manner as other acetabular reamer cups, with the exception that because of its relatively low cost, the acetabular reamer cup 10 of the invention may be discarded after a single surgical use rather than being cleaned and reused.

Several embodiments of the disposable acetabular reamer cup of the invention were destructively tested to determine the maximum torque which could be withstood by the reamer cup before failure. Conventionally, these cups are essentially spherical in shape with a radius from about 40 mm to about 80 mm. Six acetabular reamer cups of the invention, each composed of 410 surgical stainless steel provided with a ⅛" thick disk of LEXAN polycarbonate joined together by four equally separated detents and complementary intrusions as illustrated in the drawings were tested by attaching the same into a tool driver of the type disclosed in U.S. Pat. No. 4,811,632. The tool driver was clamped in a vise whereby the longitudinal axis of the tool driver and the axis of rotation of the acetabular reamer cups were essentially vertical. A ⅛" hexagonal machine nut was welded coaxially of each acetabular reamer cup. A conventional torque wrench was then applied to the nuts and each of the acetabular reamer cups of the invention were torqued until failure. The torque registered at failure was recorded. Half of the acetabular reamer cups tested were torqued in a clockwise direction. The other half of the acetabular reamer cups of the invention were torqued in a counterclockwise direction. The test results are indicated below.

Failure occurred in each case by the plug 14 separating from the bowl 12. All of the plugs tested failed between 300 and 342 inch-pounds. The average inch-pounds at failure was 327.33 inch-pounds. The plugs tested failed as follows:

Plug 1 failed at 326 inch-pounds in clockwise rotation
Plug 2 failed at 342 inch-pounds in counterclockwise rotation
Plug 3 failed at 300 inch-pounds in clockwise rotation
Plug 4 failed at 340 inch-pounds in counterclockwise rotation
Plug 5 failed at 336 inch-pounds in clockwise rotation
Plug 6 failed at 320 inch-pounds in counterclockwise rotation Referring to FIGS. 5 through 8, the disposable cutter 40 of the invention has a bowl 50 and cutting lid 74. Bowl 50 has bottom 62, an upstanding wall 66 and a top 54. Bowl 50 is essentially cylindrical in shape. Bowl bottom 62 has an opening 64 therein. Bowl 50 defines a longitudinal axis 70. Cutting lid 74, bowl 50 and bottom opening 64 are each coaxially arranged on axis 70. In a particular embodiment, bowl 50 is made of a polymeric material and is transparent. The polymeric material of bowl 50 in all embodiments is strong and lightweight. In specific embodiments, the polymeric material is preferred to have high temperature or impact resistance. An example of such a material having these properties is a polycarbonate sold under the trademark LEXAN by E. I. Dupont de Nemours and Company. Opening 64 has flange 65 about its perimeter. Flange 65 is integral with upstanding wall 66 and is congruous with the shape of opening 64.

Cutting lid 74 is substantially disc-shaped and has a plurality of cutting edges 82 extending upwardly from lid 74 and spirally or radially arranged in a pattern. A debris passage 84 adjoins each cutting edge 82 immediately forwardly thereof in the intended direction of rotation. Debris passages 84 extend through cutting lid 74.

Cutting edges 82, in the specific embodiment shown, are straight and generally parallel to the top of the cutting lid 74. Cutting edges 82 are generally radial of cutting lid 74. In another specific embodiment, cutting edges 82 are spirally arranged on the cutting lid 74. In all embodiments, cutting edges 82 are positioned to extend over the entire surface of cutting lid 74. In a specific embodiment, there are two cutting edges 82 in generally diametrically opposite positions which cover the same territory. Cutting edges 82 are also positioned to overlap each other. In a specific embodiment, the overlap is about fifty percent of the length of the cutting edges 82.

Each of the cutting edges 82 are preceded by a debris passage 84 as above mentioned. The specific purpose of these debris passages 84 will be mentioned hereinafter. In the specific embodiment shown, each debris passage 84 is semi-circular in shape. However, in other embodiments, these debris passages 84 may be rectangular, square, or shaped as otherwise desired. In a specific embodiment, cutting edges 82 are equally spaced over cutting lid 74. In the specific embodiment illustrated in FIG. 3, each cutting edge 82 is positioned on a radii about 35° to about 55° apart from adjacent cutting edges 82 and from about 0.25 to about 0.375 inches long. All of the cutting edges are equally spaced from cutting lid 74. In a specific embodiment, this spacing of cutting edges 82 is from about 0.03 to about 0.04 inches.

In a specific embodiment, cutting lid 74 and cutting edges 82 are of 19 gauge (0.040) 410 surgical stainless steel. Cutting lid 74 is formed as disclosed in U.S. Pat. No. 4,811,632 entitled "Method of Producing An Acetabular Reamer Cup", the specification of which is incorporated herein by reference.

In a specific embodiment, opening 64 is hexagonally shaped in order to receive a tool driver. In another specific embodiment, opening 64 is octagonally shaped in order to receive a tool driver as aforementioned and disclosed in allowed U.S. patent application Ser. No. 07/696,949 and U.S. Pat. No. 5,171,312; the specifications of which are incorporated herein by reference.

Notches 90 and rivots 94 solely secure cutting lid 74 to top 54 of bowl 50. In all of the embodiments of the invention, there is a plurality of congruous notches. In the specific embodiment illustrated, these notches are oppositely disposed. Each of the notches have two parts. In the embodiment illustrated, cutting lid 74 has female notch cutouts 96 with opposed upstanding edges 100 and a bottom edge 102. Bowl 50 has upstanding male notch portions 104 having opposed notch edges 106 and a bottom edge 108. Male notch portions 104 and female notch portions 96 are complementary such that when cutting lid 74 is placed on bowl 50, male notch portions 104 totally fill female notch portions 96. In this assembled condition, bottom edges 102 mate with and are flush with bottom edges 108. Functionally, bottom edges 102 and 108 insure that the cutting lid 74 is coaxial with bowl 50 and maintain that relationship during use.

On the other hand, opposed edges 100 and 106 bear the cutting forces applied to each of the cutting edges generally perpendicularly to radii of the cutting lid 74. Therefore, opposed edges 100, 106 must have sufficient area and must be spaced sufficiently far apart to provide male notch portions 104 with sufficient strength to withstand these forces. In a specific embodiment made of LEXAN polycarbonate, it has been found that if male notch portions have a dimension measured circumferentially from about 0.25 to about 0.35 inches and a thickness measured radially of cutting lid 74 of about 0.06 to about 0.08 inches, cutting lid 74 can withstand torques measured under destructive testing as above described from about 300 to about 340 inch-pounds.

As there is no appreciable force on notch bottom surfaces 102 and 108, neither the surface area of the bottom notches or the radial thickness of notches 90 is determined by the forces opposed by bottom notch surfaces 102 and 108.

Rivots 94 are provided to oppose the forces tending to separate cutting lid 74 and bowl 50. Rivots 94 comprise a rivot bore 110 in cutting lid 74 and a rivot spike 112 of bowl 50. Rivot spike 112, in a specific embodiment, is molded integrally with bowl 50. When the cutting lid 74 is secured to bowl 50, rivot spike 112 is positioned in rivot bore 110 and rivot spikes 112 are enlarged at their distal ends so as to hold cutting lid 74 and bowl 50 together as is well known in the prior art. In a specific embodiment, rivot spikes 112 can be enlarged by applying heat to the spikes. In another specific embodiment, rivots 94 can be substituted by pins, screws or other fasteners. Since rivots 94 are not relied upon to resist the torque forces above mentioned, rivot spikes 112 and rivot bores 110 can be relatively small as they are not relied upon to oppose any major forces of any appreciable size. In a specific embodiment, rivot spikes 112 and rivot bores 110 have a diameter of about 0.100 to 0.150 inches. In all embodiments, both notches 90 and rivots 94 are congruous.

In operation, a tool driver (not shown) such as those described in the referenced patent applications and patents, is positioned in opening 64 and is made to rest on flange 65. The polygonal shape of opening 64 insures that bowl 50 with cutting lid 74 secured thereto will rotate with tool driver as desired. With the cutting lid 74 positioned on the tool driver, the tool driver, the cutting lid 74, the bowl 50 all rotate about the same axis. Inasmuch as each of the cutting edges 82 and the debris passages 84 are provided in pairs and equally spaced from the center thereof, cutting lid 74 and bowl 50 are each balanced about axis 14 such that when rotated about axis 14, no vibration occurs.

The patella cutters of the invention are utilized to shave bone from the inside of the patella when operating on the knee of a person. Debris cut from the patella by the cutting edges 82 pass through the debris passages 84 and are deposited within the bowl 50. At various times during the operation, cutting lid 74 may be removed and the debris may be removed from bowl 50 and a new cutting lid 74 may be positioned on tool driver 10. This may occur several times during a single operation inasmuch as the patella is one of the hardest bones of the human body. The bone debris cut from the patella by the patella cutting system of the invention is saved to be later used during the operation in accordance with standard surgical procedures.

As cutting lid 74 is brought into contact with the patella, cutting edges 82 begin to slice and cut bone debris therefrom. When cutting lid 74 is rotated, debris passages 84 precede cutting edges 82 so that bone shavings of bone and debris removed from the patella by cutting edges 82 proceed through debris passages 84 to lodge in bowl 50. The bone debris passes through debris passages 84 into bowl 50. In the specific embodiment having transparent bowls 50, the operator is able to see the accumulation of bone debris and tissue matter through bottom 62 of bowl 50. This enables the operator to know precisely what cutting edges 82 are removing, namely tissue or bone.

Cutting edges 82 with debris passages 84 are spacially arranged on top 78 of cutting lid 74. Cutting lid 74 can be cleaned, sharpened and reused or discarded as the case may be. The disc shape of the cutting lid 74 allows cutting lid 74 to be manufactured relatively inexpensively and is generally provided as being disposable. Disposability of the cutting lid 74 allows the cutting lid 74 to be furnished to surgeons in a sterile pack, thereby eliminating concern over the desired aseptic conditions of the operating room.

With the patella cutter of the invention, the patella may be left with a smoothly cut, essentially planar surface utilizing the cutting lid 74 of the invention. With the cutting edges 82 covering the total surface of the cutting lid 72, upon rotation of the invention the improved patella cutting system improves upon the cutting tolerances. Heretofore, normal tolerances were about 0.03 inches. Cutting tolerances with the improved patella cutting system of the invention are within 0.010 inches. In specific embodiments, each cutting edge 82 is positioned on a radii or angularly thereto as desired.

Upon completion of operation, bowl 50 can be easily removed from the tool driver, and the debris used as desired. The bowl 50 can then be discarded or cleaned as desired. In the case that bowl 50 with cutting lid 74 is not going to be discarded, the curved shaped of bottom 62 facilitates cleaning and prevents dried blood and debris from being trapped within interior 58 of bowl 50.

Disposable cutting lid 40 provides a disposable cutting lid that can be used on a variety of tool drivers without the use tools. Bowl 50, being transparent, enables the operator to see into interior 58 thereby assisting in the overall efficiency of the operation and also functions to reduce human error. Bowl 50 is made of polymeric material and is therefore inexpensive to manufacture, light, and yet durable. Cutting lid 74 is a simple disc shape and does not require numerous manufacturing steps, but rather can be done in only a single stamping, thereby making disposable cutting lid 40 much less expensive to manufacture.

The improved acetabular reamer cup 10 and the improved cutting lid 74 of the invention provide disposable surgical tools which fit on a tool driver with a minimum of free play, light in weight, relatively inexpensive and quick and easy to install from a tool driver.

While a specific embodiment of the invention has been shown and described herein for purposes of illustration, the protection afforded by any patent which may issue upon this application is not strictly limited to the disclosed embodiment; but rather extends to all structures and arrangements which fall fairly within the scope of the claims which are appended hereto:

What is claimed is:

1. A disposable cutter comprising a cutting lid having a plurality of cutting edges, said cutting lid having perforations adjoining said cutting edges, said cutting lid defining an axis of rotation, said cutting lid being joined to the top of a transparent bowl, said bowl having a bottom with a tool driver opening therein, said opening being coaxial with said bowl and said cutting lid.

2. The disposable cutter of claim 1 wherein said bowl is joined to said cutting lid by at least one pair of oppositely disposed congruous notches in the top of said bowl and said cutting lid respectively.

3. The disposable cutter of claim 1 wherein said bowl is joined to said cutting lid by at least one pair of oppositely disposed rivots in said lid and said bowl.

4. The disposable cutter of claim 1 wherein said bowl is joined to said cutting lid by at least one pair of oppositely disposed congruous notches and rivots in the top of said bowl and said cutting lid respectively.

5. The disposable cutter of claim 1 wherein said bowl is formed of polymeric material.

6. The disposable cutter of claim 1 wherein said cutting edges are radial of said lid.

7. The disposable cutter of claim 1 wherein said cutting edges upon rotation of said cutting lid about said axis each sweep an area overlapped by other of said cutting edges a total of about one and one-half times.

8. The disposable cutter of claim 1 wherein said tool driver opening is hexagonal.

9. The disposable cutter of claim 1 wherein said tool driver opening is octagonal.

10. The disposable cutter of claim 1 wherein said bowl can transmit to said cutting lid a torque of more than 300 inch-pounds in a first direction of rotation coaxial with said bowl and a torque of more than 300 inch-pounds in a second direction of rotation opposite in handedness to said first direction of rotation coaxial with said bowl.

11. The disposable cutter of claim 1 wherein said cutting lid has an exterior generally planar surface and cutting edges are substantially parallel to said surface of said cutting lid and are disposed to cut upon rotation of said body.

12. The disposable cutter of claim 1 wherein said cutting edges are spirally arranged.

13. A disposable cutter comprising a generally cylindrical hollow body having a top and an interior and a bottom and an upstanding wall and a longitudinal axis, a disc-shaped cutting lid secured to said top of said body, said cutting lid having cutting edges extending from said lid, said cutting lid having debris passages therein, said bottom having an opening for receiving a tool driver therein.

14. The disposable cutter of claim 13 wherein said body is composed of a polymeric material.

15. The disposable cutter of claim 13 wherein said cutting body is joined to said cutting lid by at least one pair of oppositely disposed congruous notches and at least one pair of oppositely disposed rivots in the top of said body and said cutting lid respectively.

16. The disposable cutter of claim 13 wherein said body can transmit to said cutting lid a torque of more than 300 inch-pounds in a first direction of rotation coaxial with said body and a torque of more than 300 inch-pounds in a second direction of rotation opposite in handedness to said first direction of rotation coaxial with said body.

17. The disposable cutter of claim 13 wherein said cutting edge are substantially parallel to said surface of said cutting lid and are disposed to cut upon rotation of said body.

18. The disposable cutter of claim 13 wherein said cutting edges are spirally arranged.

19. The disposable cutter of claim 13 wherein said bottom opening is hexagonally shaped.

* * * * *